United States Patent
Sinfield et al.

(10) Patent No.: US 9,863,881 B2
(45) Date of Patent: Jan. 9, 2018

(54) METHODS FOR MEASURING CONCENTRATIONS OF ANALYTES IN TURBID SOLUTIONS BY APPLYING TURBIDITY CORRECTIONS TO RAMAN OBSERVATIONS

(71) Applicant: Purdue Research Foundation, West Lafayette, IN (US)

(72) Inventors: Joseph Victor Sinfield, West Lafayette, IN (US); Chukwukelue Kenneth Monwuba, Baltimore, MD (US)

(73) Assignee: PURDUE RESEARCH FOUNDATION, West Lafayette, IN (US)

(*) Notice: Subject to any disclaimer, the term of this patent is extended or adjusted under 35 U.S.C. 154(b) by 277 days.

(21) Appl. No.: 14/597,614

(22) Filed: Jan. 15, 2015

(65) Prior Publication Data
US 2015/0198534 A1 Jul. 16, 2015

Related U.S. Application Data

(60) Provisional application No. 61/927,705, filed on Jan. 15, 2014.

(51) Int. Cl.
*G01N 21/65* (2006.01)
*G01N 15/06* (2006.01)
(Continued)

(52) U.S. Cl.
CPC ............ *G01N 21/65* (2013.01); *G01N 15/06* (2013.01); *G01N 21/274* (2013.01);
(Continued)

(58) Field of Classification Search
CPC ...... G01N 21/65; G01N 21/274; G01N 21/51; G01N 21/4738; G01N 15/06;
(Continued)

(56) References Cited

U.S. PATENT DOCUMENTS 7,486,398 B1* 2/2009 Cole ...................... G01N 21/39
356/432
2006/0008382 A1* 1/2006 Salamitou ......... B01L 3/502715
422/400

(Continued)

OTHER PUBLICATIONS

Barman, Ishan et al. "Turbidity Corrected Raman Spectroscopy for Blood Analyte Detection." Analytical chemistry 81.11 (2009): 4233-4240.*

(Continued)

*Primary Examiner* — Dominic J Bologna
(74) *Attorney, Agent, or Firm* — Purdue Research Foundation

(57) ABSTRACT

A method of measuring the concentration of an analyte in a turbid solution containing the analyte and a solvent is disclosed. The method includes determining a turbidity value for the turbid solution based on a Raman line intensity calibration data set for the solvent. The method further includes determining turbidity correction factor based on the turbidity value and a Raman line calibration data set for the analyte and applying the turbidity correction factor to the Raman line intensity of the analyte in the turbid solution and calculating a turbidity-corrected Raman line intensity for the analyte in the turbid solution. The turbidity-corrected Raman line intensity of the analyte in the turbid solution is then used to determine the concentration of the analyte in the turbid solution utilizing previously developed calibration data sets relating Raman line intensity to analyte concentration in solutions of negligible turbidity.

20 Claims, 10 Drawing Sheets

(51) Int. Cl.
  *G01N 21/27* (2006.01)
  *G01N 21/47* (2006.01)
  *G01N 21/51* (2006.01)
(52) U.S. Cl.
  CPC ......... *G01N 21/4738* (2013.01); *G01N 21/51* (2013.01); *G01N 2015/0693* (2013.01); *G01N 2021/4709* (2013.01); *G01N 2021/656* (2013.01)
(58) Field of Classification Search
  CPC ......... G01N 2021/4709; G01N 21/656; G01N 2015/0693
  See application file for complete search history.

(56) References Cited

U.S. PATENT DOCUMENTS

| | | | |
|---|---|---|---|
| 2007/0291263 A1* | 12/2007 | Lipson | A61B 5/0059 356/301 |
| 2008/0062417 A1* | 3/2008 | Stave | G01J 3/44 356/301 |
| 2011/0307183 A1* | 12/2011 | Galiano | G01N 21/61 702/19 |

OTHER PUBLICATIONS

Bloch, J., et al., Field Test of a Novel Microlaser-Based Probe for in Situ Fluorescence Sensing of Soil Contamination. Applied Spectroscopy, vol. 52(10), 1299-1304 (1998).
Sinfield, J.V., et al., Effects of Soils on Laser Induced Fluorescence of BTX Contaminated Pore Waters. J. Geotech. Geoenviron. Eng. 1999.125:1072-1077.
Kram, M.L. et al., DNAPL Characterization Methods and Approaches, Part 1: Performance Comparisons. Ground Water Monit. R. (GWMR), 109-123 (2001).
Pasteris, J. D., et al., Raman Spectroscopy in the Deep Ocean: Successes and Challenges. Applied Spectroscopy 195A-208A (2004).
Battaglia, T.M., et al., Development of an in situ fiber optic Raman system to monitor hydrothermal vents. Analyst, 1 2 9 , 6 0 2-6 0 6 (2004).
Moore, T. S., et al., Marine Chemical Technology and Sensors for Marine Waters: Potentials and Limits. Annu. Rev. Mar. Sci. 2009. 1:91-115.
Soos, M., et al., Interpretation of Light Scattering and Turbidity Measurements in Aggregated Systems: Effect of Intra-Cluster Multiple-Light Scattering. J. Phys. Chem. B 2009, 113, 14962-14970.
Wind, L. and Szymanski, W.W. Quantification of scattering corrections to the Beer—Lambert law for transmittance measurements in turbid media. Meas. Sci. Technol. 13 (2002) 270-275.
Berrocal, E. et al., Laser light scattering in turbid media Part I: Experimental and simulated results for the spatial intensity distribution. Optics Express, 2007, vol. 15, 10649-10665.
Ivanov, A.P. et al., Application of Lasers in Oceanographic Investigations (Review). J. Appl. Spectrosc. 1982, 37(4): 1097-1103.
Phillips, D.M., et al., Effect of Water Turbidity on Laser Depth Sounding Performance. In: M.F. Penny and D.M. Phillips (Eds.), Proceedings, Fourth Laser Hydrography Symposium, Adelaide (Australia). Sep. 30-Oct. 3, 1980. Document AR-002-576. Report ERL-0193-SD, 336-346 (1981).
Hoge, F.E. et al., Airborne detection of oceanic turbidity cell structure using depth-resolved laser-induced water Raman backscatter. Applied Optics, 1983, vol. 22, No. 23 , 3778-3786.
Amann, H., Laser Spectroscopy for Monitoring and Research in the Ocean. Physica Scripta. vol. T78, 68-72, 1998.
Marshall, B.R., et al., "Raman scattering and in-water ocean optical properties." Appl. Opt. 1990, 29(1): 71-84.
Omar, A-F, et al. "Turbidimeter Design and Analysis: A Review on Optical Fiber Sensors for the Measurement of Water Turbidity." Sensors. 2009. 9(10): 8311-8335.
Vellekoop, I.V., et al, "Scattered light fluorescence microscopy; imaging through turbid layers." Opt. Lett. 2010. 35(8): 1245-1247.
Schulmerich, M.V. et al. "Subsurface Raman spectroscopy and mapping using a globally illuminated non-confocal fiber-optic array probe in the presence of Raman photon migration." Appl. Spectrosc. 2006. 60(2): 109-114.
Barman, I, et al. "Turbidity-corrected Raman spectroscopy for blood detection." Anal. Chem. 2009. 81(11):4233-4210.
Matousek, P. et al. "Depth profiling in diffusely scattering media using Raman spectroscopy and picosecond Kerr gating". Appl. Spectrosc. 2005. 59(2): 200-205.
Matousek, P. "Raman signal enhancement in deep spectroscopy 626 of turbid media." Appl. Spectrosc. 2007. 61(8):845-854.
Eliasson, M. et al. "Deep subsurface Raman spectroscopy of turbid media by a defocused collection system." Appl. Spectrosc. 2007. 61(10): 1123-1127.
Braunlich, G., et al. "Detection of Pollutants in water by Raman Spectroscopy." Water Res. 1973. 7(11): 1643-1647.
Rossabi, J., et al. "Field tests of a DNAPL characterization system using cone penetrometer-based Raman spectroscopy." Ground Water Monit. R. 2000. 20(4): 72-81.
Downing, B.D. et al. "Seeing the light: The effects of particles, dissolved materials, and temperature on in situ measurements of DOM fluorescence in rivers and streams." Limnol. Oceanogr-Meth. 2012. 10: 767-775.
Everall, N. et al. "Picosecond time resolved Raman spectroscopy of solids: capabilities and limitations for fluorescence rejection and influence of diffuse reflectance." Appl. Spectrosc. 2001. 55(12): 1701-1708.
Schulmerich, M.V. et al. "Subsurface Raman spectroscopy and mapping using a globally illuminated non-confocal fiber-optic array probe in the presence of Raman photon migration" Appl. Spectrosc. 2005. 60(2): 109-114.
Yang, J. et al. "Quantitative Raman spectrometry: The accurate determination of analytes in solution phase of turbid media." Chemometr. Intell. Lab. 2013. 126:6-10.
Zonios, G., et al. "Light scattering spectroscopy of human skin in vivo." Opt. Express. 2009. 17(3): 1256-1267.
Enejder, A.M. et al. "Blood analysis by Raman spectroscopy." Opt. Letters. 2002. 27(22):2004-2006.
Corlu, A. et al. "Three-dimensional in vivo fluorescence diffuse optical tomography of breast cancer in humans." Opt. Express. 2007. 15(11): 6696-6716.
Yaqoob, Z. et al. "Optical phase conjugation for turbidity suppression in biological samples." Nat. Photonics. 2008. 2: 110-115.
Popoff, S.M. et al. "Measuring the Transmission Matrix in Optics: An Approach to the Study and Control of Light Propagation in Disordered Media." Phys. Rev. Lett. 2010. 104(10): 100601.1-4.
Wu, J., et al. "Analytical model for extracting intrinsic fluorescence in turbid media." Appl. Optics, 1993. 32(19), 3585-3595.
Muller, M.G., et al. "Intrinsic fluorescence spectroscopy in turbid media: Disentangling effects of scattering and absorption." Appl. Optics, 2001. 40(25): 4633-4646.
Weersink, R. et al. "Noninvasive measurement of fluorophore concentration in turbid media with a simple fluorescence/reflectance ratio technique." Appl. Optics, 2001. 40(34): 6389-6395.
Zhang, Q., et al. "Turbidity-free fluorescence spectroscopy of biological tissue." Optics Lett. 2000. 25(19): 1451-1453.
Shih, W-C., et al. "Intrinsic Raman spectroscopy for quantitative biological spectroscopy Part I: Theory and simulations." Opt. Express. 2008. 16(17): 12726-12736.
Bechtel, K.L., et al. "Intrinsic Raman spectroscopy for quantitative biological spectroscopy Part II: Experimental applications." Opt. Express 2008. 16(17): 12737-12745.
Reble, C., et al. "Quantitative Raman spectroscopy in turbid media." J. Biomed. Opt. 2010. 15(3), 037016-1-037016-8.
Mylvaganam, S., et al. "Turbidity sensor for underwater applications: Sensor Design and System Performance with Calibration Results", In: Proceedings OCEANS '98, Sep. 28-Oct. 1, 1998, 1:158-161.
Tipton, T.L., et al. "Self-referencing fiber-optics fluorescence sensor for turbid samples." J. Environ. Eng.-ASCE. 1998. 124(6): 545-548.

(56) References Cited

OTHER PUBLICATIONS

Bristow, M., et al. "Use of water Raman emission to correct airborne laser fluorosensor data for effects of water optical attenuation." Appl. Optics, 1981. 20(17): 2889-2906.

Monwuba, C.K., et al. "Geoenvironmental Influences on Raman Spectroscopic Monitoring of Chlorinated Solvent Natural Attenuation." [Doctoral Thesis Dissertation]. West Lafayette, Indiana: Purdue University, 2013.

Heller, W., et al. "Theoretical investigations on the light scattering of colloidal spheres. I. The specific turbidity." J. Chem. Phys. 1957. 26: 498-506.

Paul, C.J., et al. "Impact of turbidity on TCE and degradation products in ground water." Ground Water Monit. R. 1997. 17(1): 128-133.

* cited by examiner

METHODS FOR MEASURING CONCENTRATIONS OF ANALYTES IN TURBID SOLUTIONS BY APPLYING TURBIDITY CORRECTIONS TO RAMAN OBSERVATIONS

CROSS-REFERENCE TO RELATED APPLICATIONS

The present U.S. patent application is related to and claims the priority benefit of U.S. Provisional Patent Application Ser. No. 61/927,705, filed Jan. 15, 2014, the contents of which hereby incorporated by reference in their entirety into the present disclosure.

STATEMENT REGARDING GOVERNMENT FUNDING

This invention was made with government support under CMMI0927112 awarded by the National Science Foundation. The government has certain rights in the invention.

TECHNICAL FIELD

The present disclosure generally relates to methods and apparatus for analyzing the composition of materials, and in particular for correcting Raman signals of liquids containing suspended particles.

BACKGROUND

This section introduces aspects that may help facilitate a better understanding of the disclosure. Accordingly, these statements are to be read in this light and are not to be understood as admissions about what is or is not prior art.

Improvements in diode laser, fiber optic, and data acquisition technologies are enabling increased use of Raman spectroscopic techniques for both in-lab and in-situ water analysis. In this disclosure "in-situ" is used to describe a situation in which the measurement or action is or can be performed directly at the source of a solution or sample in the field. Thus in this disclosure "in-situ" can be used interchangeably with each of "in the field", "on-site, "in-line" and "in-flow". Aqueous media encountered in the natural environment often contain suspended solids that can interfere with spectroscopic measurements. Removal of these solids, for example via filtration, can have adverse effects on the extent to which subsequent measurements are representative of actual field conditions under which the aqueous media are collected. Turbidity is a measure of the loss of optical transparency of a medium resulting from the presence of suspended solids or other interfering matter, which can limit the overall sensitivity of optical spectroscopic methods and make it challenging to perform quantitative analysis.

Turbidity is measured by various methods known to those skilled in the art and is typically measured in NTUs (Nephelometric Turbidity Units). NTUs provide a standardized measure of the extent to which white light is scattered at an angle of 90° from the direction of the incident beam by particles suspended in a liquid relative to the same effect observed in a standard solution containing the polymer reaction byproduct of hydrazine sulfate and hexamethylenetetramine, in accordance with Environmental Protection Agency (EPA) Method 180.1, and are a standard measure of water quality in environmental science.

The adverse influence of turbidity on optical spectroscopic measurements is recognized in many fields. In oceanographic investigations, the challenges posed by turbidity for in-situ spectroscopic analyses have been acknowledged for several decades. Studies have indicated that turbidity limited the effectiveness of studies of petroleum films, chlorophyll distribution, and sea water temperature and salinity performed using airborne laser sounding. In a similar domain, a reduction in the Raman backscatter of water with increasing turbidity in airborne examinations of water optical transmission was observed. It has been reported that turbidity can adversely impact potential to measure low concentrations of natural and hazardous chemicals in the ocean. In the context of environmental science, several researchers have indicated that the presence of suspended particulates in open fresh water and groundwater can lead to scattering, absorption, and displacement of an unknown sample volume that would otherwise be interrogated by optical sources in a spectroscopic system and can thus lead to inaccurate measurements of in-situ chemical concentrations.

Several attempts have been made to apply correction to Raman observations affected by turbidity. Some researchers desire to see "through" the turbid medium to perform spectroscopic analysis on underlying layers of material. This is the case in many biological scenarios and studies of pharmaceuticals. In these contexts, researchers have developed techniques to 1) work with the limited amount of unaffected light returned from a turbid sample (e.g., confocal microscopy or multiphoton microscopy, often at considerable complexity and expense, 2) invert the scattered return, sometimes employing sophisticated time gating, with tradeoffs in resolution peer "through" turbid layers via what has been termed interferometric focusing with the limitation of a need for a priori access to the target focal plane, 4)) employ non-linear chemometricor or bioinformatic methods to address non-analyte specific signal variances stemming from turbidity through techniques such as support vector regression, after considerable experimental trials or work with simulated samples.

Some studies focused on studying the bulk turbid material itself—that is the matrix responsible for generating the turbidity effect in the sample—which in many applications is granular or powdery in nature (e.g., bulk active pharmaceutical ingredient analysis). Here again time-resolved scattering observations can be employed to discern the source of scattered return as a function of the probable scattered photon path length, or a spatial offset between the incident illumination source and the collected return can be employed to reassemble an image from diffusely scattered light. In addition, researchers have highlighted the merits of employing a large interrogation spot size and making use of reflecting mirrors or diffuse reflectors to enhance Raman returns when the scattering medium is of analytical interest. Still other researchers perform analyses of liquid (water) or tissue samples and wish to study the chemical composition of the fluid or tissue via quantitative analysis of the medium in which the turbid inducing constituents are suspended (more narrowly, the Raman scatterers within the turbid medium). In these contexts, differing methods have been employed for different target materials, with notable variations in approach between the laboratory and the field.

For analysis of biological tissues in the laboratory, where turbidity correction is arguably the most advanced, corrections were initiated in the context of fluorescence studies. Here researchers recognized that fluorescent and diffusely reflected photons behave in a similar manner in turbid media, and methods were derived to obtain what is termed "intrinsic fluorescence"—that is the fluorescence emanating from direct excitation incidence on the target—from either the ratio of measured fluorescence to diffuse reflectance at a given emission wavelength, or through interpretation of photon migration models of concomitantly measured fluorescence and reflectance.

A similar line of logic was employed by researchers in the development of intrinsic Raman spectroscopy (IRS) and turbidity-corrected Raman spectroscopy (TCRS) which are both based on the photon migration approach and employ alternate acquisition of Raman and diffuse reflectance spectra to obtain corrected Raman observations. The IRS method employs a Monte Carlo calibration model based on extensive analysis of phantom media representative of target constituents, as well as accurate knowledge of constituent Raman scattering coefficients. The TCRS method overcomes these limitations through a theoretical link between the observed Raman spectrum, the diffuse reflectance spectrum, and the turbidity-corrected Raman spectrum. The method, however, requires complex calibration to obtain an instrument specific constant, determination of the average photon path length in the turbid media under investigation, and estimation of the diffusely reflected light at the Raman excitation frequency. Some studies have suggested turbidity corrections based on the relationship between Raman return and sample reflectance, but distinguish the contributions of absorption and scattering, and employ a Monte Carlo simulation to obtain a corrected Raman signal from an inferred combination of the target material absorption coefficient and reduced scattering coefficient. Although complex, and challenging to implement in a natural field setting, the breakdown of the influences of turbidity on Raman observations provided by these model-based corrections reveal that for quantitative characterization of turbid media, turbidity-induced variations in sampling volume—that is the turbidity inducing constituents occupy a fraction of the interrogated sample volume—often become dominant over other forms of spectral distortion (absorption and scattering).

This premise has historically been exploited in the natural environment where turbidity corrections have been primarily linked to direct or indirect measurements of sample turbidity that provide an indication of combined scattering, absorption, and volume reduction effects. Some researchers corrected measurements of fluorescent tracers in model aquifers for turbidity related signal attenuation through cyclic excitation of target media and a known fluorescence reference positioned on the far side of a flow through sampling vessel, enabling real time correction for signal amplitude, with the known drawback of potential interference from fluorophores within the target media. Others put forward a simple groundwater fluorometer signal intensity correction based on an empirically derived relationship between sample turbidity level and related changes in scattered excitation energy. Some researchers corrected UV/VIS absorption measurements of paper mill wastewater for turbidity by a theoretical relation linking turbidity to light attenuation based on an assumption of the diameter of the turbidity inducing particles, and a spectral correction relating changes in scattering at any given wavelength to turbid particle diameter. Others demonstrated the potential to correct observations of fluorescing dissolved organic matter for turbidity effects through instrument specific calibration of excitation light absorption as a function of dissolved organic matter content in target media, and empirically derived relations between field derived turbidity levels and fluorescence signal attenuation, noting the need for periodic collection of water samples and measurement of filtered samples in the laboratory to assess the appropriate magnitude of the correction.

As outlined above prior attempts to correct for the adverse effects of turbidity rely on one or more of the following: pass-through optical observations, a priori modeling of the test medium, significant excitation penetration into a sample, the opportunity to excite and collect optical energy at displaced locations, and/or large area optical excitation and/or collection, or optical behavior characterized by the Beer-Lambert law. Generally, few of these conditions, if any, can be met in a typical in-situ field monitoring scenario. Thus a need exists for methods of correcting for turbidity effects in Raman observations in practical monitoring scenarios in the field without the need for "pass through" optical observations, without the need for a priori modeling thus enabling corrections in "real time" thereby accounting for in-situ changes, and without the need to deeply penetrate the sample with radiation or analyze large areas, thus enabling corrections in "real time" to account for in-situ changes, and enabling targeted, single-sided optical observations.

SUMMARY

A method for measurement of concentration of at least one specified analyte in a solution of unknown turbidity containing a solvent and at least one specified analyte is disclosed. This method is applicable when the analyte has negligible effect on a Raman line intensity of the solvent. The method includes providing a solution of unknown turbidity containing a solvent and at least one specified analyte and a first calibration data set that relates turbidity of an analyte-free solvent sample to a Raman line intensity for the analyte-free solvent. The method further includes the step of generating Raman signature of the solution and determining a Raman line intensity of the solvent in the solution and a Raman line intensity of the at least one specified analyte in the solution. Further, the method includes comparing the Raman line intensity of the solvent in the solution to the first calibration data set and determining a turbidity value for the solution. The method further includes providing a second calibration data set that relates turbidity of the at least one specified analyte to a normalized Raman line intensity for the at least one specified analyte. Next step in the method is to determine a turbidity correction factor based on the turbidity value of the solution and the second calibration data set. Then, the turbidity correction factor is applied to the Raman line intensity for the at least one specified analyte in the solution and a turbidity-corrected Raman intensity for the at least one specified analyte is calculated. The concentration of the at least one specified analyte in the solution is then determined by comparing the turbidity-corrected Raman intensity of the at least one specified analyte to a calibration curve that relates Raman intensity of the at least one specified analyte to concentration of the at least one specified analyte in a solvent with negligible turbidity.

Another method for measurement of concentration of at least one specified analyte in a solution of unknown turbidity containing a solvent and at least one specified analyte is disclosed. This method is especially suitable when the analyte has non-negligible effect on a Raman line intensity of the solvent. The method includes providing a solution of unknown turbidity containing a solvent and at least one specified analyte and generating Raman signature of the solution and determining a Raman line intensity of the solvent in the solution and a Raman line intensity of the at least one specified analyte in the solution. The method further includes providing a calibration data set that relates turbidity of the at least one specified analyte to a normalized Raman line intensity for the at least one specified analyte. The method also includes measuring the turbidity value of the solution. Next step in the method is to determine a turbidity correction factor based on the turbidity value of the solution and the calibration data set. Then, the turbidity correction factor is applied to the Raman line intensity for the at least one specified analyte in the solution and a turbidity-corrected Raman intensity for the at least one specified analyte is calculated. The concentration of the at least one specified analyte in the solution is then determined by comparing the turbidity-corrected Raman intensity of the at least one specified analyte to a calibration curve that relates Raman intensity of the at least one specified analyte to concentration of the at least one specified analyte in a solvent with negligible turbidity.

BRIEF DESCRIPTION OF DRAWINGS

While some of the figures shown herein may have been generated from scaled drawings or from photographs that are scalable, it is understood that such relative scaling within a figure are by way of example, and are not to be construed as limiting.

DETAILED DESCRIPTION

Figure 1:
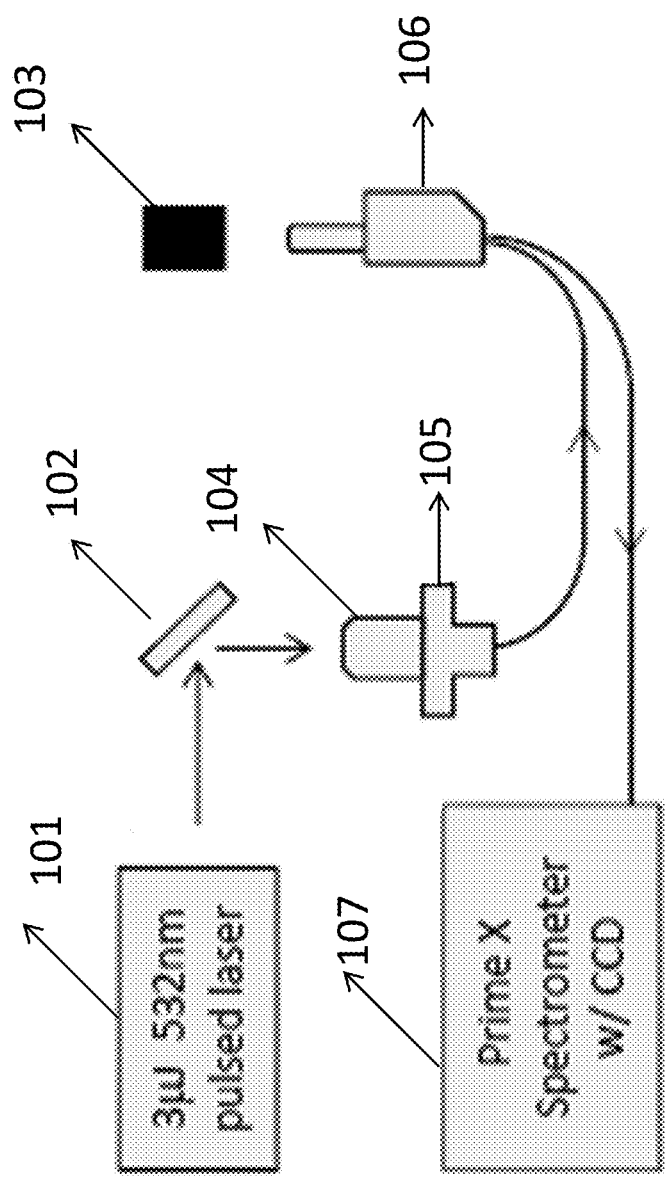
FIG. 1 is a schematic representation of a 3 µJ Raman measurement system.

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended, such alterations and further modifications in the illustrated device, and such further applications of the principles of the disclosure as illustrated therein being contemplated as would normally occur to one skilled in the art to which the disclosure relates.

The turbidity correction methods put forward in this disclosure are particularly amenable, but not limited, to in-situ environmental applications of Raman spectroscopy which are often performed down-hole in a monitoring well, through an optical window in direct contact with soil beneath the ground surface via an in-situ probe, or in a submersible unit deployed in open water. These types of measurements typically employ a 180° backscatter single-sided acquisition geometry making use of correction techniques that rely on passing light "through" a sample ineffective. In addition, the conditions monitored, especially when probing the ground or in open water, are constantly changing making use of a priori modeling impractical. Further, the depth of penetration of light into what is often very turbid media, or water within the pore space of soil, is often quite limited and thus techniques that rely on long optical path lengths or separate excitation from collection locations tend to be unreliable. Beyond this, the desire to observe chemicals in the water at relatively low concentrations (on the order of parts per million to parts per billion), and ultimately to limit interference from naturally occurring fluorophores, encourages use of a small irradiated spot size to both a) maximize the energy incident on the target per unit area (with the area often constrained by the pore size of a soil matrix) and b) limit the return path length of the detected energy to reduce convolution of Raman and fluorescence returns and enable time-resolved analysis.

With the above consideration in mind, the correction methods of this disclosure inherently account for absorption and volume reduction effects of turbidity, and can be performed in real-time, based on spatially relevant in-situ turbidity information with even limited signal from constrained optical spot size.

Studies leading to this focused on evaluation of turbidity effects on Raman spectroscopic measurements of two common environmental pollutants in aqueous solution—ammonium nitrate, and trichloroethylene. The former is typically encountered in the run-off from agricultural operations and is a strong scatterer that has no significant influence on the Raman spectrum of water. The latter is a commonly encountered pollutant at contaminated sites associated with degreasing and cleaning operations, and is a weak scatterer that has a significant influence on the Raman spectrum of water.

Raman observations of each compound in aqueous solutions of varying turbidity created by doping samples with silica flour with grain sizes ranging from 1.6-5.0 µm were employed to develop relationships between observed Raman signal strength and turbidity level. Shared characteristics of these relationships were then employed to define generalized correction methods for the effect of turbidity on Raman observations of compounds in aqueous solution.

Turbidity has been shown to adversely influence the intensity of Raman spectroscopic observations of nitrate and TCE in aqueous solution, with a consistent trend of natural logarithmic decreases in Raman return with linear increases in turbidity. The form of the relationship is significant in that it highlights that turbidity induces significant changes in Raman return intensity at field relevant turbidity values. This trend appears consistent regardless of turbidity-inducing grain size over a tested grain size range of 1.6 to 5.0 µm.

A correction approach relating water Raman signatures to turbidity and in turn to the influence of turbidity on analyte signatures has been determined to adjust Raman measurements on turbid samples for the presence of suspended solids in situations in which the analyte and/or sample background do not influence the vibrational modes of water. This approach provided reliable indications of actual liquid phase analyte concentrations with less than 10% error. Turbid sample Raman measurements for systems containing an analyte that does influence the vibrational modes of water still appear to follow a predictable reduction in intensity as a function of turbidity and could potentially be corrected by employing direct turbidity observations or diffuse reflectance measurements.

Two compounds were examined as target analytes in laboratory prepared aqueous solutions: ammonium nitrate and trichloroethylene (TCE). Ammonium nitrate, which has little impact on the Raman vibrational modes of water, was used as a relatively innocuous contaminant in extensive parametric studies of the effect turbidity level and turbidity inducing soil grain size on analyte Raman observations. The ammonium nitrate employed in this study was obtained from VWR (Product #BDH0212, ACS Grade, 95%). Trichloroethylene (TCE), a chlorinated hydrocarbon and member of a group of compounds known as dense non aqueous phase liquids, was employed in a narrower set of tests as an analyte known to influence the Raman vibrational modes of water. A spectrometric grade (purity>99.5%) of the compound obtained from Alfa Aesar was used as received for this work. It is understood that reference to ammonium nitrate and TCE are by way of example only, and not to be construed as limiting any of the embodiments shown and discussed herein for the measurement of analyte concentrations in-situ.

In order to minimize the influence of chemical or physical interactions that might occur between the turbid inducing media employed in this study and the compounds in aqueous solution, relatively inert homogenous silica flour was used to create the turbid samples (CAS No. 14808-60-7). The material is white to tan in color, has a specific gravity of 2.65, and is approximately 99.0-99.9% $SiO_2$, <0.8% $Al_2O_3$, <0.1% $Fe_2O_3$, <0.1% $TiO_2$ by weight. This material, which was commercially sourced from AGSCO Corporation, Wheeling, Ill., had been sieved to obtain distinct samples, each with a well-defined grain size distribution containing at least 80% of one of the following grain sizes: 1.6, 2.1, 2.4, 3.5 and 5.0 µm, as specified by the manufacturer. When employed as suspended particles in aqueous solutions in the tests described below, these samples are referred to simply by their prominent grain size. It is understood that such description of particles are but one example, and are not to be considered limiting on any of the embodiments. For example, particles other than silica can be used to induce turbidity. Non-limiting examples include metallic and organic substances.

Aqueous samples of ammonium nitrate solutions were prepared by adding the desired amount of reagent grade ammonium nitrate ($NH_4NO_3$) by weight to a single liter of deionized water and mixing thoroughly. All solution concentrations were verified by copper-cadmium reduction method known to those skilled in the art. Aqueous solutions of trichloroethylene were prepared in a 40-ml amber colored glass vial topped with a Teflon-coated silicone rubber septa sealed and screwed in place with a cap. All preparations were undertaken at room temperature (24.5° C.). The 40 ml bottles were filled with deionized water to a capacity of 20 mL and then neat TCE was placed at the base of the vials through the use of a disposable pipette. This helped to ensure that no bubbles were introduced in the process, which was stopped when the supernatant water was overflowing. The vials were then capped and sealed immediately avoiding headspace and preventing loss due to vaporization. These vials were then shaken and allowed to settle to equilibrium for at least three days.

To prepare dilute concentrations, aliquots were taken through the use of a syringe and injected into a closed vial containing deionized water in an appropriate volume needed to make a particular concentration based on a mass balance calculation. Final concentrations were validated using a GC-dry electrolytic conductivity detector (DELCD) in combination with a photo ionization detector (PID) (SRI8610C Chassis).

Turbid samples were prepared by introducing known masses of silica flour into pre-prepared trichloroethylene aqueous samples in 30-ml clear glass vials, sealed with zero headspace using Teflon caps. These masses were varied to create turbidity values ranging between 0-250 NTU. While turbidity encountered in the natural environment tends to range from 0-50 NTUs, higher values were also explored to assess the consistency of observed trends and better model observed behavior. All solutions contained particle sizes with terminal velocities long enough to remain stable for spectroscopic analysis, based on Stokes Law. These mixtures were manually shaken and allowed to settle for a time period of 2-24 hr, prior to testing. Turbidity measurement was done with a HACH 2100P Turbidimeter. Samples were prepared in a 3.5-mL cuvette (3-Q-10-GL14C Starna Cells Inc.) for spectroscopic analysis.

Two distinct Raman systems were employed in this study. The testing carried out with the ammonium nitrate samples made use of a closed path 532 nm 3 µJ pulsed laser (600 kHz rep rate, <0.9 ns pulse duration, Teem photonics SNG-03E-000) with a fast CCD detector. A schematic representation of the system used in this study is shown in FIG. 1. Referring to FIG. 1, the 3 µJ pulsed laser 101 is coupled into a 532 nm Raman probe (Inphotonics) 106 which has a 90 µm excitation fiber and 105 µm collection fiber using an antireflection coated mirror 102, 10× objective lens 104 and a multimode fiber coupler 105. The probe is focused on the sample cuvette 103 and scattered light is collected in a 180 degrees back scatter configuration back into the fiber probe 106. The collection fiber is then coupled directly to a CCD spectrometer 107 (BWTek Prime X). Raman signal intensity at any given wavelength was obtained as the output of the 1024×58 CCD array as observed by the BWSpec software for a total integration time of 120 s. Although various systems are shown and described for making measurements of the Raman signals, it is understood that these systems are by way of example only, and various embodiments of the present invention contemplate the use of any system or methods for acquiring the Raman measurements.

Figure 2:
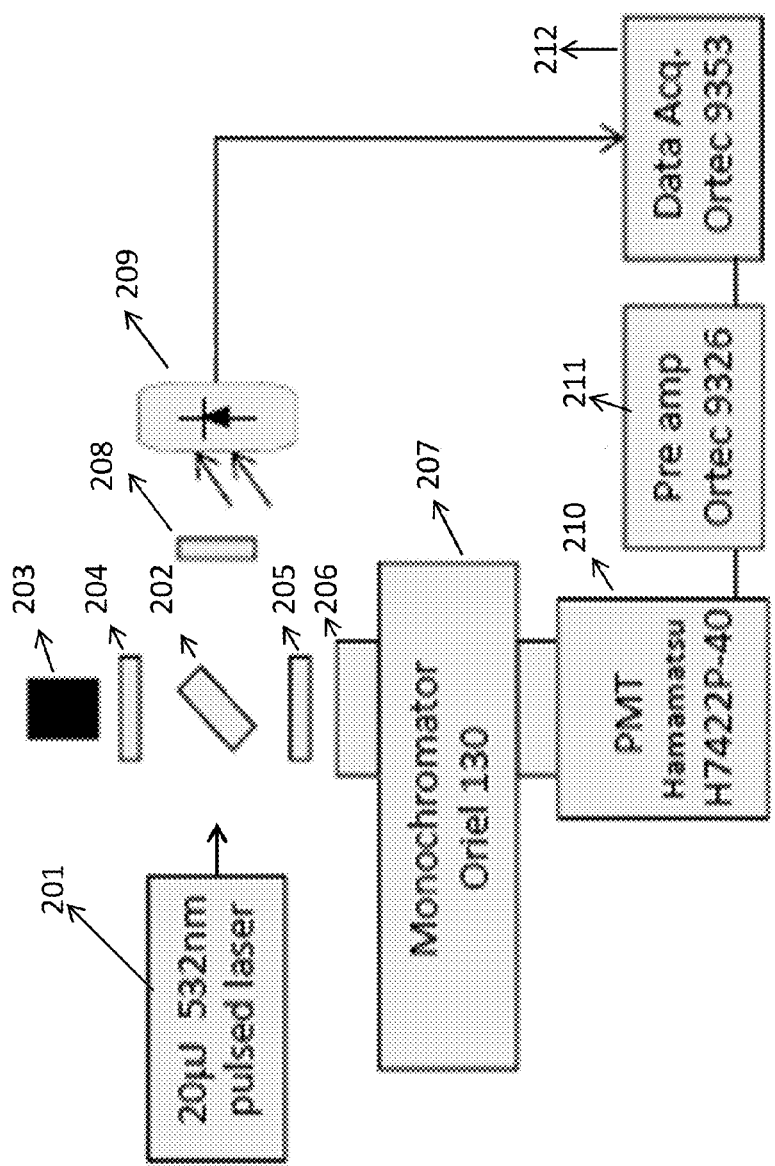
FIG. 2 is a schematic representation of a 20 µJ Raman measurement system

For tests involving TCE, which has a smaller Raman cross-section than ammonium nitrate, greater laser power was used as shown in FIG. 2. Referring to FIG. 2, these test were performed with an open-path 532 nm 20 µJ pulsed laser (2 kHz repetition rate; ~0.4 ns pulse duration, Teem photonics PNG-002025-100). Here the 20 µJ excitation beam 201 is directed to an Ø 25.4 mm dichroic laser beam filter (Edmund Optics) at 45 degree angle of incidence 202 which directs the excitation energy into an optical train that focuses the energy on a sample cuvette 203. Within the optical train a Ø 45 mm AR aspheric lens 204 with Numerical Aperture (NA) 0.612 (Thorlabs) focuses the excitation on the sample and serves as a collection and focus optic for the 180 degree back scattered Raman photons from the sample back through the dichroic filter 202 to a Ø 50.8 mm AR achromatic doublet lens 205 (Thorlabs) with NA of 0.17. The achromatic lens in turn focuses Raman photons on the entrance slit of a monochromator 207 (Oriel 130 ⅛ m, with flat-ruled 1200 lines/mm grating blazed at 500 nm). A 532 nm Ø 25.4 mm long-pass filter is placed at the monochromator entrance slit 206 to eliminate source wavelength background. Energy passing directly through the dichroic filter is focused through a convex lens 208 and used to create a data acquisition trigger via a photodiode 209. Light passing through the monochromator is observed using a photomultiplier tube (PMT) (Hamamatsu H7422-40P) 210 operated in a photon counting mode. The PMT is observed via an impedance matched link to a pre-amplifier (Ortec 9326, operated at a gain of 20×) 211 and a 100-ps binned comparator (Ortec 9353) 212. For all experiments performed with this system, spectra were collected with 25 μm slits, a step size of 0.1 nm, and 120 s observation time per wavelength.

Figure 3:
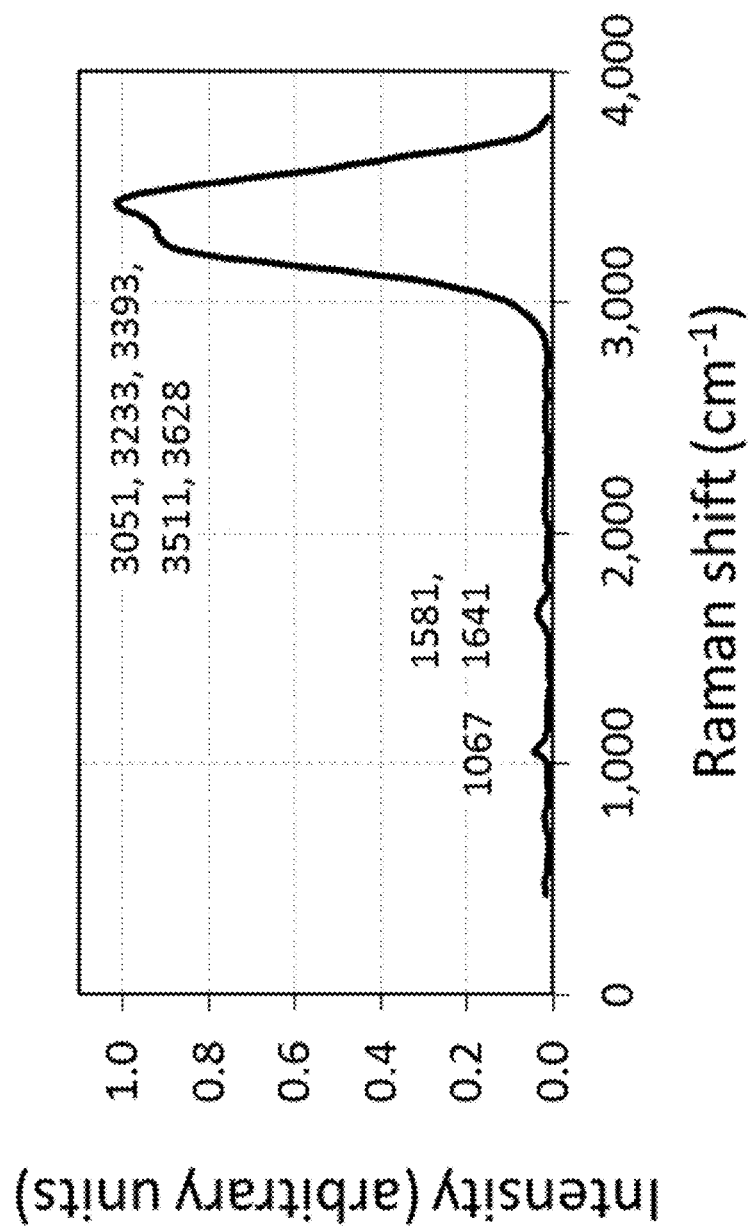
FIG. 3 is a Raman spectrum of a 2000 ppm aqueous nitrate sample.

Referring to FIG. 3, the turbidity related Raman analyses presented herein pertaining to ammonium nitrate focused on observing the $NO_3^-$ symmetric stretching peak at 1067 $cm^{-1}$ and the intermolecular OH stretching mode of water at 3393 $cm^{-1}$. However, it is understood that measurements at these specific wavelengths are by way of example only, and various embodiments of the present invention contemplate the observation of other wavelengths of water, and still further the observation of any analyte wavelength of interest.

Three aqueous concentrations of ammonium nitrate were studied: 2000, 3500, and 6800 ppm nitrate-N under varying turbidity levels. While these concentrations are generally higher than those found in the environment (researchers have reported field concentrations as high as 2000 ppm), their use facilitated improved signal to noise in the analyses allowing observation of even subtle trends in the relationship between sample turbidity level and Raman signal strength.

Figure 4:
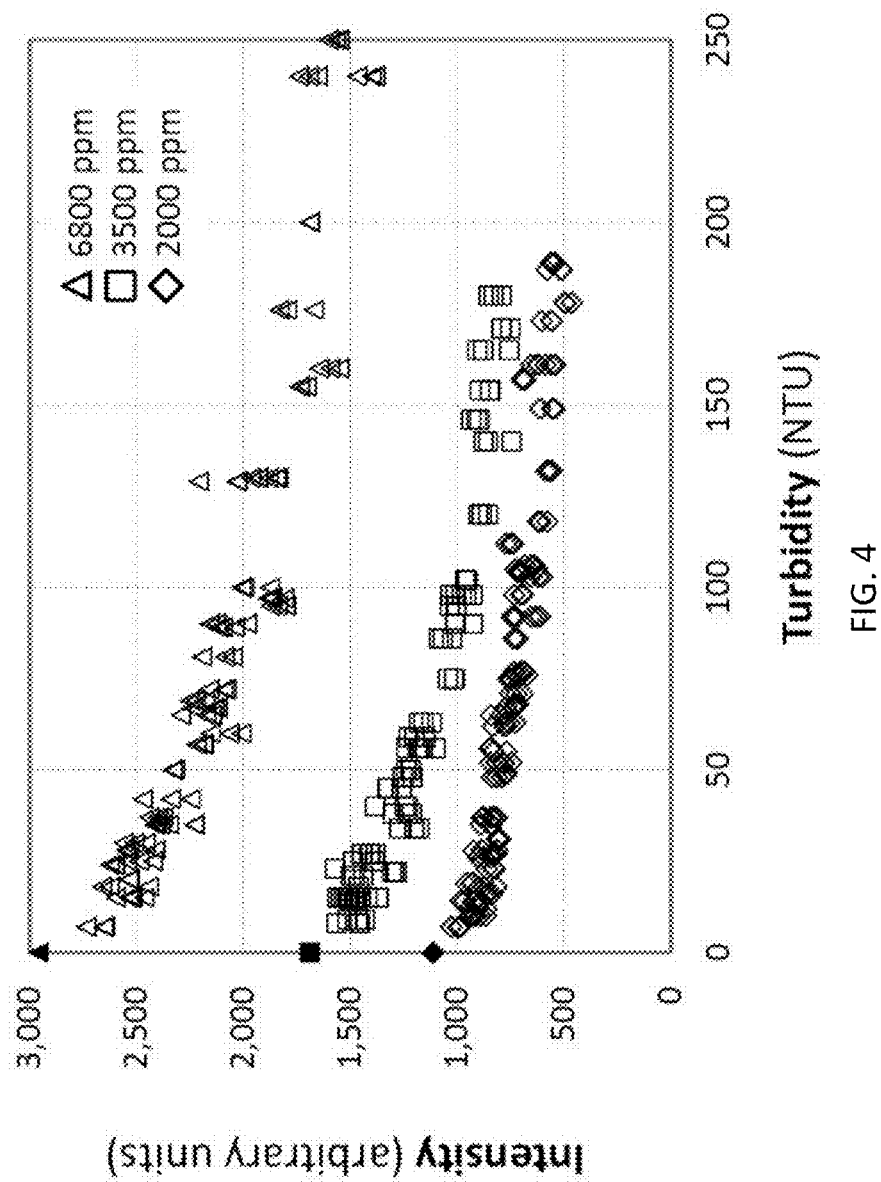
FIG. 4 is a representation of intensity of ammonium nitrate Raman line (1067 $cm^{-1}$) as a function of turbidity (NTU) for varying aqueous nitrate solution concentrations.

Results of the Raman analyses of the silica doped ammonium nitrate solutions are presented in FIG. 4. Open symbols represent turbid solutions, and the solid symbols represent average intensities in negligible turbidity, or reference, solutions. In this disclosure negligible turbidly implies low turbidity values in the range of 1-2 NTUs. Negligible turbidity can be set to be higher NTU values depending on the accuracy desired in the final analyte concentration values. The spread in the data tends to increase at higher nitrate concentrations as would be anticipated due to the fact that variability in Raman intensity typically scales with the square root of absolute intensity. For all three studied nitrate concentrations, the intensity of the $NO_3^-$ Raman return tends to drop rapidly over the field relevant NTU range (0-50±NTU) and then decline more gradually at higher NTU values.

Figure 5:
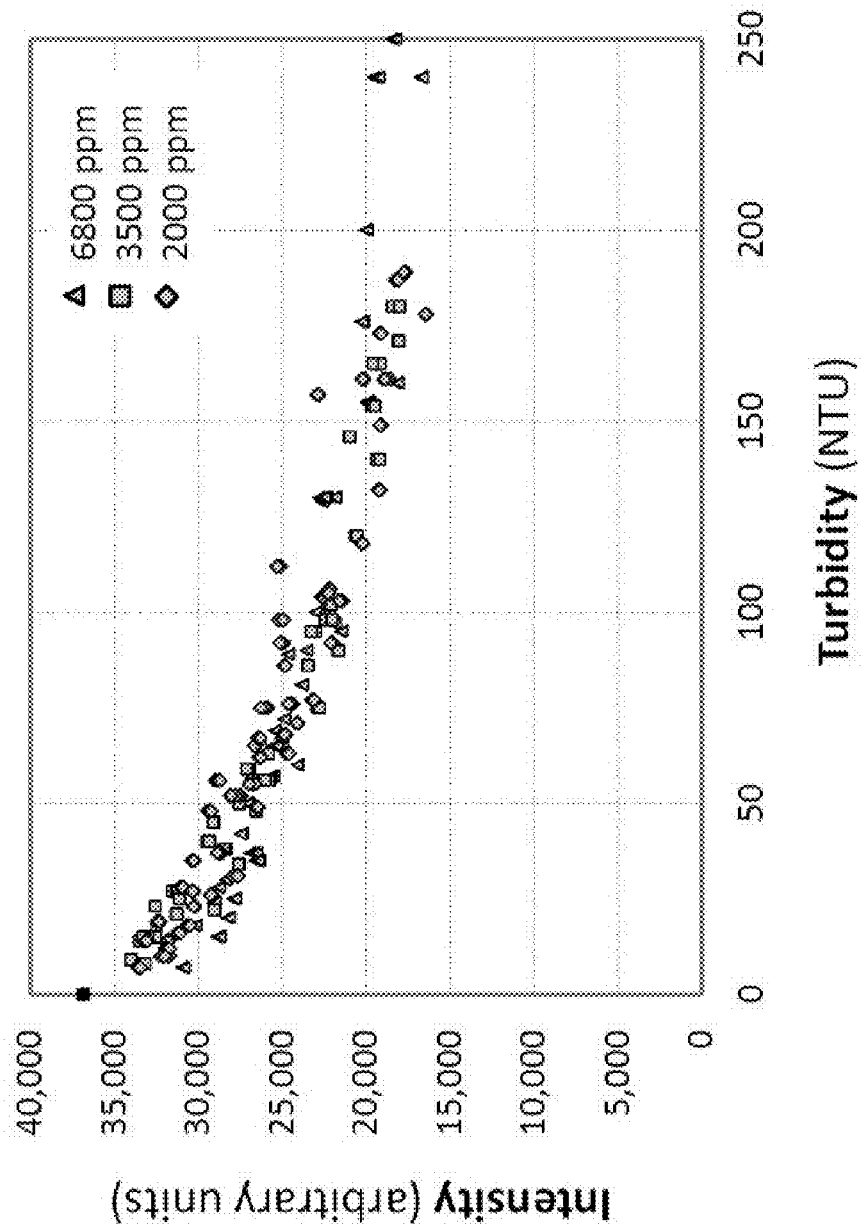
FIG. 5 is a representation of Raman intensity of the OH stretching line (3393 $cm^{-1}$) of water in ammonium nitrate aqueous solution as a function of turbidity (NTU).

A similar trend is noticed in the intensity of the OH water stretching Raman return at 3393 $cm^{-1}$, as shown in FIG. 5. FIG. 5 shows a Raman intensity of the OH stretching line (3393 $cm^{-1}$) of water in ammonium nitrate aqueous solution as a function of turbidity (NTU). Overall, the presence of suspended fine silica flour with grain sizes in the range of 1.6-5.0 μm has a detrimental impact on the intensity of the Raman observations. However, unlike the NO3− signal intensity which varied in magnitude in relation to the ammonium nitrate concentrations, the nitrate concentration in solution has no discernible impact on the observed variation in the intensity of the OH stretching line at 3393 $cm^{-1}$ over the studied nitrate concentration range. At negligible turbidity, the water line intensity remained consistent within +/−1.5%. This observation can be attributed to the fact that the Raman vibrational modes of the water are unaffected by the presence of the nitrate at these levels. The observed yet insignificant variation at negligible turbidity is likely attributable to expected fluctuations in Raman line intensity which are known to be on the order of the square root of the number of Raman scattered photons, as well as competitive partitioning of the excitation source energy between nitrate and water molecules in solution, particularly at the higher nitrate concentrations.

Initial review of the observed trends relating Raman signal intensity and turbidity suggests that there is potential to predictably correct for turbidity's influence. However, before pursuing that avenue, it is useful to first determine if turbidity level is indeed the driving factor underlying these observations. Another potentially influential variable is the grain size of the suspended particles inducing the solution turbidity.

Figure 6:
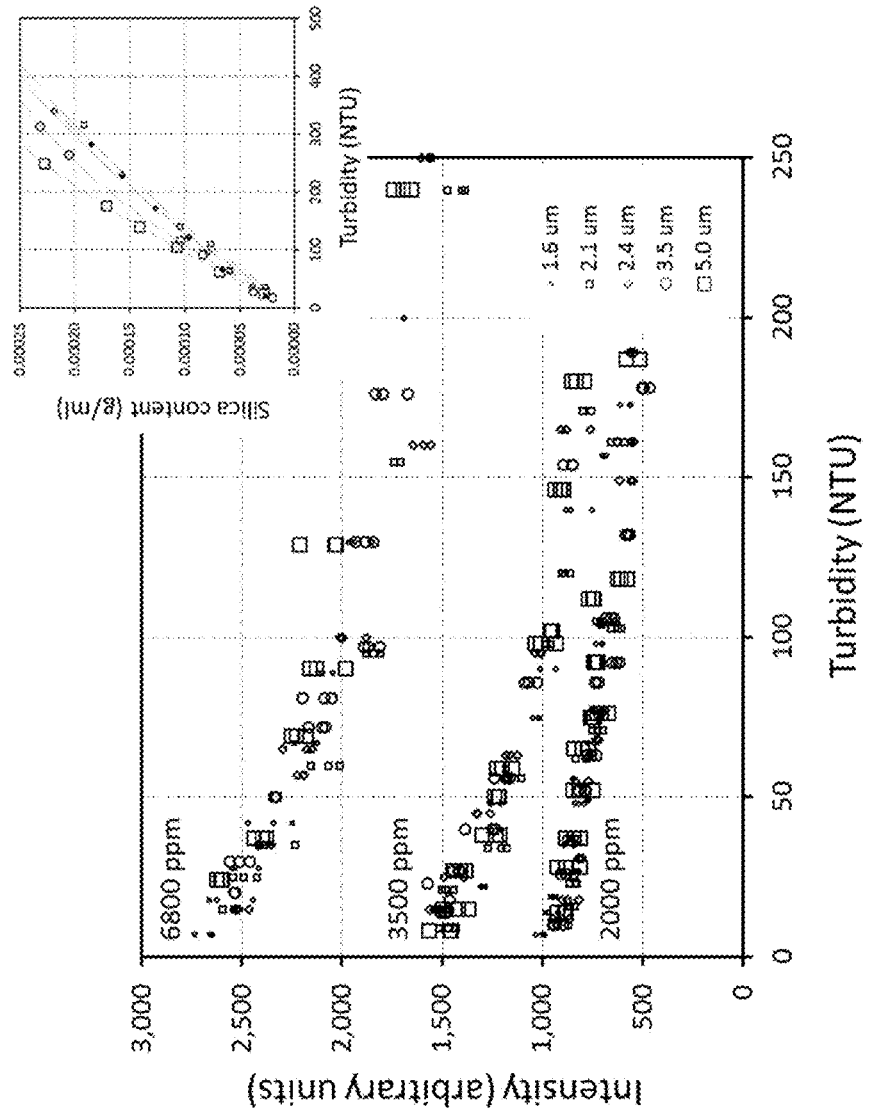
FIG. 6 presents nitrate Raman line intensity as a function of solution turbidity and turbidity-inducing silica grain size in 2000 ppm, 3500 ppm, and 6800 ppm nitrate solutions.

In order to assess the influence of suspended silica flour grain size on Raman measurements, tests were performed on aqueous ammonium nitrate solutions at varying levels of turbidity, each created with differing levels of ammonium nitrate [again, 2000, 3500, and 6800 ppm] and various ranges of suspended particle grain size [1.6, 2.1, 2.4, 3.5 and 5.0 μm]. FIG. 6 displays the intensity of the Raman nitrate line as a function of solution turbidity with silica grain size as a parameter for the 2000, 3500, and 6800 ppm nitrate solution concentrations. In addition, the inset in the upper right corner of the figure highlights the relationship between observed turbidity levels and the silica content in the tested solutions (g/ml).

From FIG. 6, it is clear that the intensity of the nitrate Raman return decreases with increasing turbidity for all three ammonium nitrate concentrations studied as noted earlier. However, FIG. 6 also shows that suspended particle size has no perceptible effect on Raman signal intensity, as the intensities of the nitrate Raman return span a common range for each of the studied nitrate concentrations at any given level of turbidity regardless of the turbidity-inducing grain size. It should be noted that, with the highlighted relationship between turbidity and silica content as a function of grain size shown in the figure inset, attempts were also made to relate the Raman intensities observed at different turbidity levels to turbidity inducing silica mass per unit volume in the tested solutions as well as implied particle surface area (based on a spherical particle assumption and knowledge of particle specific gravity (2.65)). However, these perspectives had no discernible benefit over the relationship to turbidity already presented. And, of course, assessing mass or surface area of suspended particles in an actual in-field situation is impractical, while determination of turbidity is quite feasible even in single-sided test geometries as commonly pursued in field work. A similar set of analyses (not shown) for the water Raman return also shows that Raman intensity is driven by overall turbidity level and has no apparent correlation to the size of the suspended particles that induce that turbidity within the studied grain size range.

To further explore any potential relationship between the intensity of the Raman return from a turbid solution and the size of the suspended particles in the solution, additional statistical analyses were undertaken. First, a one-way General Linear Model ANOVA analysis was performed on the entire dataset using Minitab version 16. The normalized intensity of the nitrate Raman line was used as the response to changes in the studied variables, suspended particle grain size, and turbidity level, respectively. The probability, P, that turbidity level does not affect the Raman nitrate signal was 0.000, whereas the P-value for suspended particle grain size was 0.037, with α=0.05, indicating that grain size has no significant effect. An additional two-way balanced ANOVA analysis was also run by extracting a balanced data set from the overall sample at 9 narrow turbidity ranges (+/−3 NTU) for which three response observations were present for each of the five studied grain sizes. Here the probability, P, that turbidity level does not affect the Raman nitrate signal was again 0.000, whereas the P-value for suspended particle grain size was 0.448, with $\alpha=0.05$, reinforcing that at any given level of turbidity, grain size likely had no influence on nitrate Raman intensity.

From the above analysis it may be concluded that at any given level of turbidity, the grain size of the silica driving the turbidity level has little effect on the intensity Raman observations, across the studied grain size range of ~1.6-5.0 µm. This result likely stems from the narrow range of particle sizes explored here as well as the absolute size and morphology of the particles investigated which are angular in shape and have a size parameter ($\pi d/\lambda$) from ~9 (1.6 µm) to ~30 (5.0 µm), given the employed 532 nm excitation wavelength.

In this context, since turbidity level, $\tau$, is proportional to the obscured cross-section of the studied sample as defined by the relation $\tau=N\ R$ where N represents the number of suspended particles in the medium and R represents the scattering cross-section of a suspended particle, as the particle size increases, the number of particles required to achieve any given level of turbidity decreases (and vice versa), so that the total scattering cross-section of the overall sample remains approximately the same regardless of the particles used to create it. Further, given the 180 degree back-scatter configuration of the employed system, and the well-established tendency for particles larger than the wavelength of light to induce much greater scattering in the forward rather than backward direction, any changes in the particle sizes employed to achieve a given level of turbidity are likely to influence a small fraction of the back scattered light, and may have a limited impact on the net effect on Raman observations collected via the employed 180 degree backscatter optical configuration.

Figure 7:
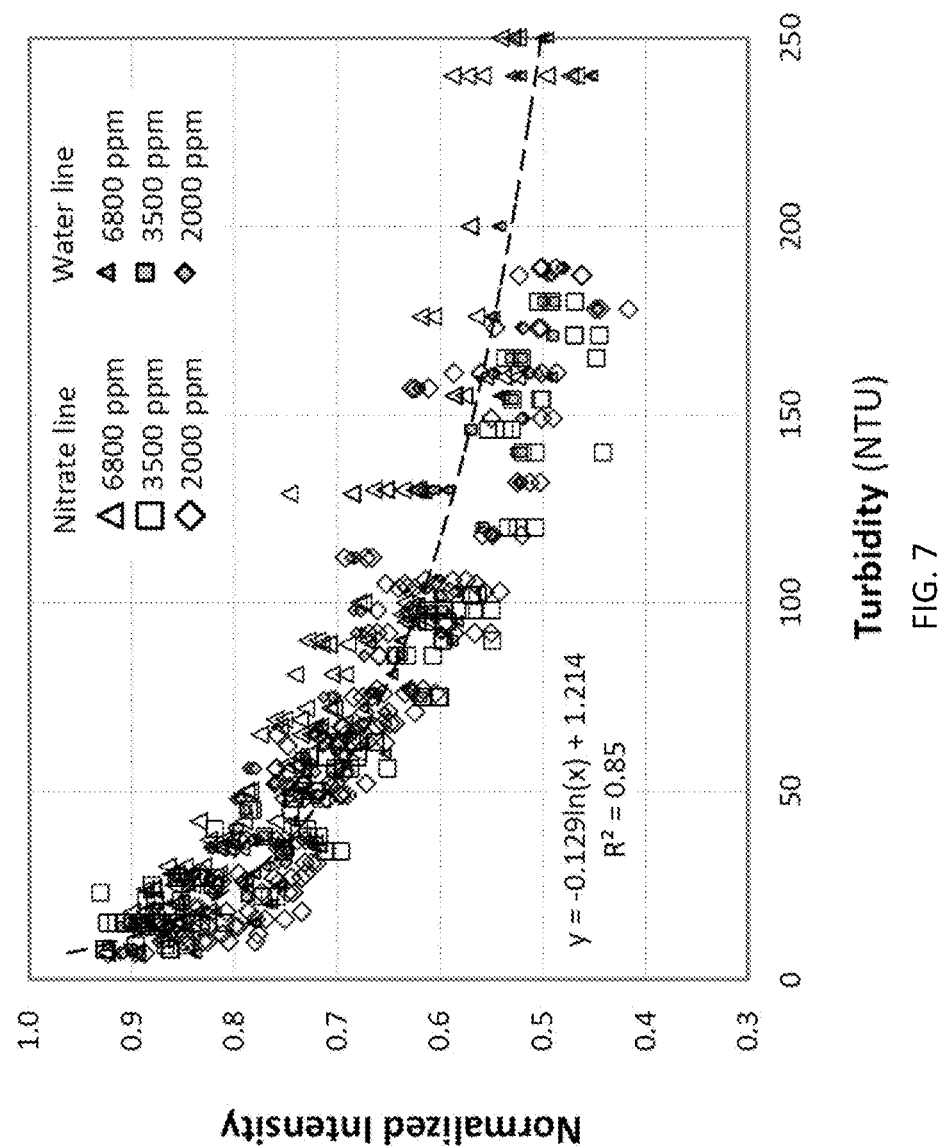
FIG. 7 is a depiction all of the turbid solution nitrate and water Raman line data from all studied nitrate solution concentrations, normalized by their respective negligible-turbidity intensities.

Based on the above analysis, the influence of turbidity on the intensity of Raman returns in the studied solutions can be modeled as a function solely of turbidity level. Thus, FIG. 7 presents all of the turbid solution nitrate and water Raman line data from all studied nitrate solution concentrations, normalized by their respective negligible-turbidity intensities. The overall data set falls into a band in which there is a rapid rate of decline in Raman intensity at low turbidity values and a slowing rate of decline at higher turbidity levels which can be best fit with a negative natural logarithmic function relating normalized Raman line intensity to turbidity level as shown in FIG. 7.

Based on theoretical considerations, one might expect the relationship between turbidity level and Raman intensity to be exponential, as the Beer-Lambert law would predict attenuation of the incident excitation energy (and thus the directly proportional Raman return) to be governed by the factor $(1-e-\tau\ l)$, where $\tau$ is the turbidity level and l is the path length of the incident energy through the sample. However, the Beer-Lambert law in its most general formulation does not account for the presence of scatterers. While this can be accommodated through use of a combined extinction coefficient (here approximated by $\tau$) that accounts for both scattering and absorption, even then there is a presumption that the scatterers in the medium meet Rayleigh ($\pi d/\lambda \ll 1$) or Mie ($\pi d/\lambda \sim 1$) criteria, depending on the formulation. As noted earlier, this is not necessarily the case here given the non-spherical shape and size parameters of the suspended particles in the tested samples. Further, the modified Beer-Lambert law also presumes that scatterers, if present, exist at low enough volume fractions that they do not induce multiple scattering phenomena. This is also unlikely to be the case in the tested samples, particularly at higher turbidity levels. Finally, the presence of the non-target suspended particles in samples tends to reduce the volume of the liquid medium that is interrogated by the incident energy, leading to a decline in observed scattering intensity from target analytes, relative to an unobstructed test volume. The net effect of these influences is that the back-scattered Raman return of the target analyte tends to decrease more rapidly with increasing turbidity level than would be predicted by a simple negative exponential relationship to turbidity level.

With the above studies and observations, methods have been developed in the present disclosure for measuring concentration an analyte in a turbid solution containing a solvent and the analyte. We now describe a method to measure the concentration of at least one specified analyte in a turbid solution of unknown turbidity containing a solvent and the at least one specified analyte. It should be recognized that a turbid solution to be studied can contain more than one analyte. The methods described here pertain to measuring the concentration one specified analyte. However, the method can be repeated for other analytes present in the turbid solution. It will be obvious to those skilled in the art that some of the measurements in the methods to be described can be done on several analytes simultaneously.

Methods can now be described for measurement of concentration of at least one specified analyte in a solution of unknown turbidity containing a solvent and at least one specified analyte. We first describe a method for a case in which the analyte does not affect the intensity of Raman line (or lines) of the solvent. This is assessed by prior studies on the solvent and solvent-analyte combinations. In this case, first a solution of unknown turbidity containing a solvent and at least one specified analyte is provided. A first calibration data set relating turbidity of an analyte-free solvent sample to a Raman line intensity for the analyte-free solvent is generated. As a non-limiting example, this data set can be generated by utilizing turbidity-inducing particles such as silica as described above. Raman signature of the solution is then generated and a Raman line intensity of the solvent in solution as well as a Raman line intensity of the at least one specified analyte in the solution are determined. The Raman line intensity for the solvent in the solution is then compared to the first calibration data set thereby determining a turbidity value for the solution. A second calibration data set that relates turbidity of the at least one specified analyte to a normalized Raman line intensity for the at least one specified analyte is generated. Normalized Raman line intensity (varying between 0 and 1) in this second calibration data set is the Raman intensity normalized with respect to the Raman line intensity of the analyte with negligible turbidity. The normalized Raman intensity in the second calibration set corresponding to the determined turbidity value for the solution can be termed turbidity normalization factor. A turbidity correction factor is then defined to be the reciprocal of the turbidity normalization factor. (For example, if the normalized Raman intensity in the second calibration set corresponding to the determined turbidity value for the solution is 0.6, then the turbidity correction factor is 1/0.6 which is 1.667.) The measured Raman line intensity of the at least one specified analyte is then multiplied by the turbidity correction factor to obtain a turbidity-corrected Raman intensity for the at least one specified analyte in the solution. Also to be generated is a calibration data set or a calibration curve that relates Raman intensity of the at least one specified analyte to concentration of the at least one specified analyte in a solvent with negligible turbidity. By comparing the turbidity-corrected Raman intensity of the at least one specified analyte to this calibration curve, the concentration of the at least one specified analyte can be determined.

According to one embodiment of this disclosure it is advantageous to obtain the analyte-free solvent sample of this method from the vicinity of the solution in the field.

It is known that nitrates have negligible effect on Raman line intensity of many solvents, especially water, and hence the above calibration methods can be employed. Negligible effect is to be understood to be effect not discernible within the accuracy of the measurements. A non-limiting example of such a nitrate which can be an analyte is ammonium nitrate and this method can be employed to determine the concentration of nitrate in a turbid solution containing ammonium nitrate. Other nitrates such as potassium nitrate can also be analyzed using the method described here. It should be recognized that potassium nitrate is a non-limiting example.

A method is now described for cases where an analyte can affect Raman line intensity of a solvent. This is assessed by prior studies on the solvent and solvent-analyte combinations. In such a case, a turbidity value for a turbid solution cannot be determined by a calibration data set such as the first calibration data set described in the above method. Instead, a turbidity value for the turbid solution is determined by a turbidity measurement. In this case, a method for measurement of concentration of at least one specified analyte in a solution of unknown turbidity with a solvent includes the following steps: a solution of unknown turbidity containing a solvent and at least one specified analyte is obtained. A calibration data set that relates turbidity of the at least one specified analyte to normalized intensity of a Raman line for the at least one specified analyte is generated. The turbidity value of the solution is measured. Normalized Raman line intensity (varying between 0 and 1) in this calibration data set is the Raman intensity normalized with respect to the Raman line intensity of the analyte with negligible turbidity. The normalized Raman intensity in this calibration set corresponding to the determined turbidity value for the solution can be termed turbidity normalization factor. A turbidity correction factor is then defined to be the reciprocal of the turbidity normalization factor. (For example, if the normalized Raman intensity in the second calibration set corresponding to the determined turbidity value for the solution is 0.6, then the turbidity correction factor is 1/0.6 which is 1.667.) The measured Raman line intensity of the at least one specified analyte is then multiplied by the turbidity correction factor to obtain a turbidity-corrected Raman intensity for the at least one specified analyte in the solution. Also to be generated is a calibration data set or a calibration curve that relates Raman intensity of the at least one specified analyte to concentration of the at least one specified analyte in a solvent with negligible turbidity. By comparing the turbidity-corrected Raman intensity of the at least one specified analyte to this calibration curve, the concentration of the at least one specified analyte can be determined.

Non-limiting examples of analytes that affect Raman line intensity of solvents such as water are chlorinated compounds and the method described here (for the case of analyte affecting Raman line intensity of solvent) can be employed. A non-limiting example of such a chlorinated compound which can be an analyte is trichloroethylene (TCE) and this method can be employed to determine the concentration of TCE in a turbid aqueous solution containing TCE. (It should be noted that if the solvent contains hydrogen bonds, then the solvent is susceptible to be affected by chlorine ions in the chlorinated compound. Thus water is affected by the chlorinated compounds.)

For the method described above where turbidity has to be measured, both direct and indirect methods can be employed. Direct methods are those where the result of the observation is a quantification of the turbidly in NTUs, or other specific measures of turbidity. A non-limiting example of such a method is the use of a turbidimeter as described in Environmental Protection Agency (EPA) Method 180.1. Indirect methods are those where an observed result has to be correlated with turbidity and the turbidity is inferred. A non-limiting example of an indirect method of measuring turbidity is the use of diffuse reflectance method, known to those skilled in the art.

To assess the effectiveness of the above methods, a series of validation tests were conducted on turbid samples with "unknown" turbidity values and varying concentrations of ammonium nitrate in water. Two concentrations were studied, 800 ppm, and 1450 ppm. In this particular case, because nitrate and water share the same curve relating normalized intensity to turbidity values, it is possible to simply normalize nitrate line intensities by the water line intensity obtained in respective tests. In this case, the error (represented by the standard deviation of the corrected observations relative to the actual concentration) between observed and actual concentrations is 4.0% and 2.2%, respectively, for the 800 ppm and 1450 ppm data sets.

In some cases however, the normalized intensity vs. turbidity curves for nitrate and water may not be the same, and it will thus be useful to employ the normalized water intensity vs. turbidity relationship to infer turbidity, and then use the nitrate normalized intensity vs. turbidity curve to estimate a turbidity correction factor for the nitrate observations. This approach is illustrated here by utilizing the normalized water intensity from each of the validation tests to obtain an estimated turbidity value that could be associated with each nitrate observation.

Figure 8:
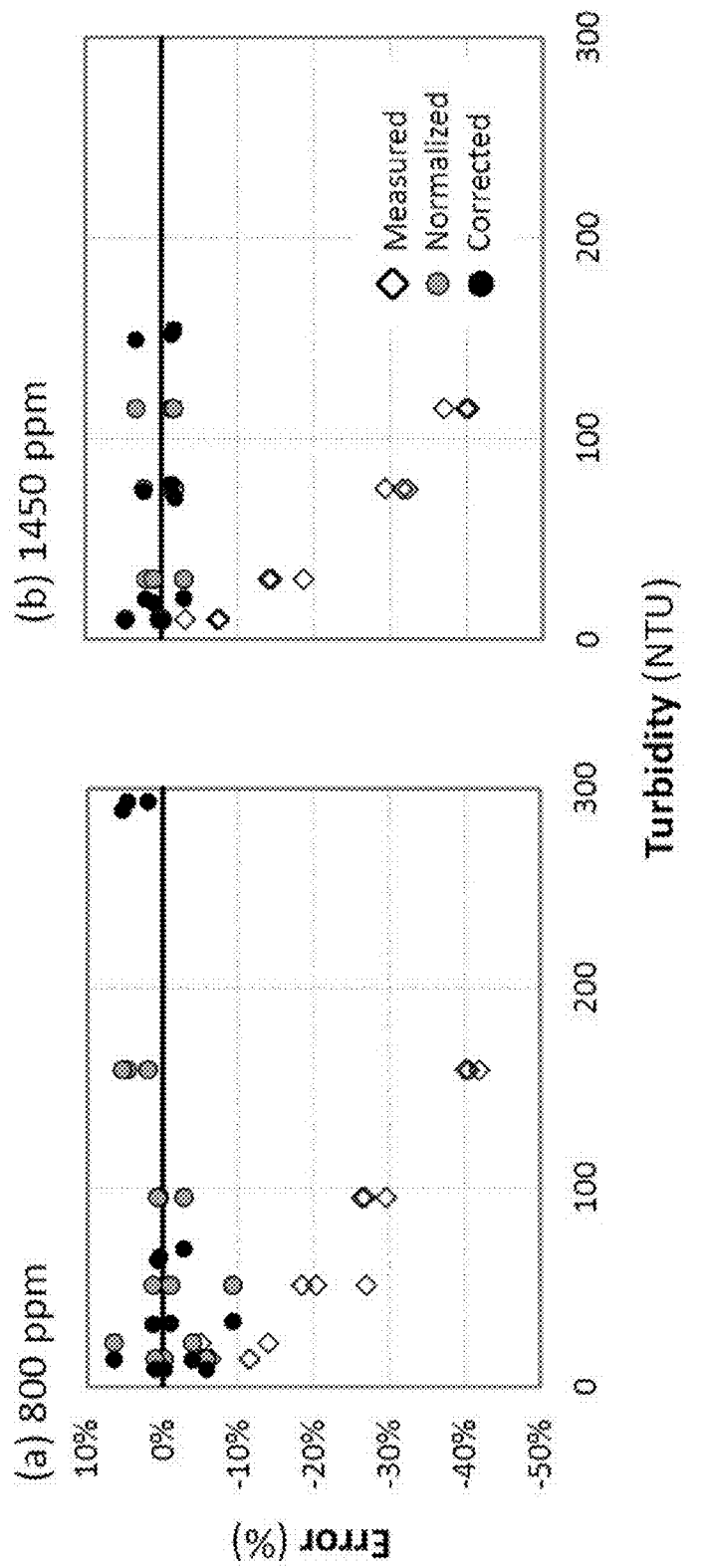
FIG. 8 is a depiction of relationship between predicted and actual nitrate concentration in turbid aqueous solutions based on turbidity correction.

FIG. 8 presents the relationship between predicted and actual nitrate concentration at the studied turbidity values, for both the 800 ppm and 1450 ppm data sets. When employing the normalized correction curves, there is error in the estimate of actual turbidity. This error is small at field relevant turbidity values, but increases significantly at higher turbidity values due to the shape of the negative natural logarithmic curve highlighted in FIG. 7, which flattens out as turbidity increases. However, this same flatness of the relationship between turbidity and normalized intensity also limits the error when turbidity is ultimately translated back into a correction factor for intensity. As a result, the error in the corrected concentrations relative to actual for the 800 ppm and 1450 ppm data sets respectively, is a maximum of −9.2% and +4.8%.

As outlined above, the corrective procedure described here can likely serve as an effective means to determine actual concentration of compounds (here ammonium nitrate) in a turbid influenced in-situ measurement scenario.

Various other embodiments of the present invention pertain to apparatus and methods for determining the effects of turbidity on time-resolved Raman spectroscopic (TRRS) measurements of TCE. Since the analyses of ammonium nitrate solutions described above revealed that variation in turbidity-inducing particle size has no significant effect on Raman observations in turbid samples for the studied grain size range, experiments here simply targeted development of a relationship between turbidity level and the intensity of the 381 cm−1 (δCH) Raman shift of TCE for turbid aqueous solutions of TCE created using silica with a grain size of 5 μm. TRRS measurements were performed using the 20 μJ open path laser configuration described earlier which makes use of a photomultiplier tube for photon detection, and thus observed intensities are reported in counts. Tests were performed on samples at varying TCE concentrations (300 ppm, 600 ppm, 900 ppm, 1200 ppm) and turbidity levels.

Figure 9:
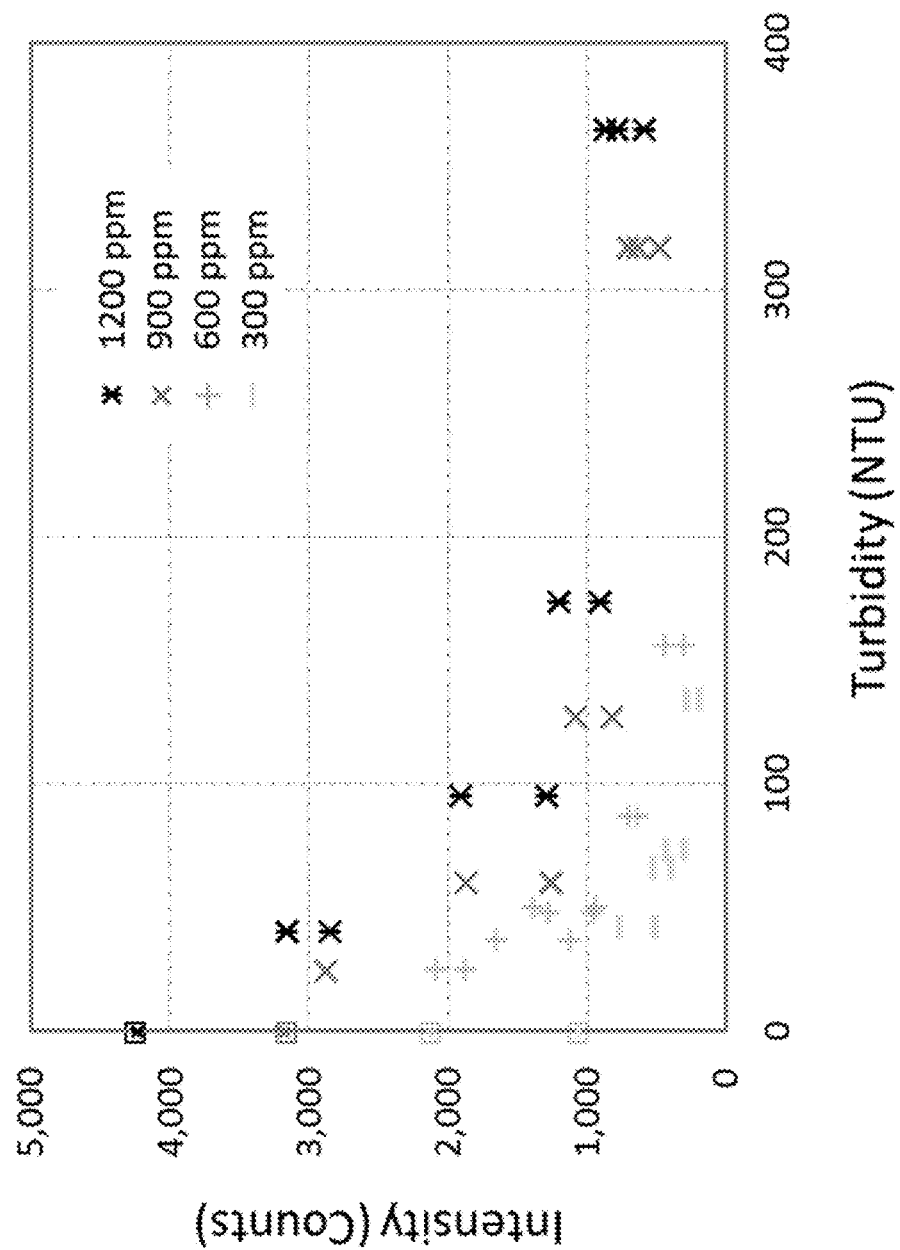
FIG. 9 is a representation of shows a normalized intensity of the δCH TCE Raman line (381 $cm^{-1}$) as a function of turbidity (NTU) for varying concentrations of TCE in aqueous solution.

FIG. 9 is a representation of shows a normalized intensity of the δCH TCE Raman line (381 cm−1) as a function of turbidity (NTU) for varying concentrations of TCE (trichloroethylene) in aqueous solution. Results on samples at varying TCE concentrations (300 ppm, 600 ppm, 900 ppm, 1200 ppm) and turbidity levels, shown in FIG. 9, are similar in trend to the prior investigation of ammonium nitrate and again reveal a rapid reduction in Raman counts as turbidity levels increase in the field-relevant range, followed by a plateau in the effect at higher turbidity levels.

Figure 10:
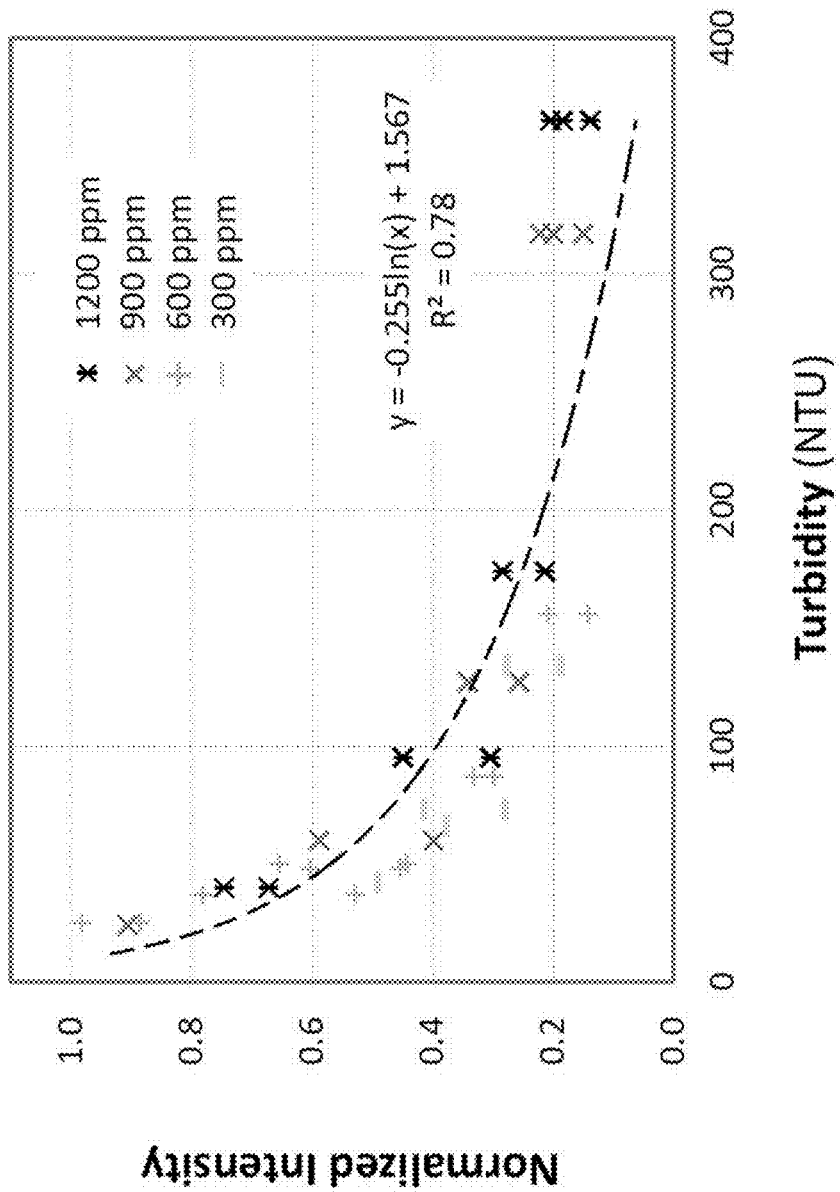
FIG. 10 is a representation of normalized intensity of δCH TCE Raman line (381 $cm^{-1}$) as a function of turbidity (NTU) for varying concentrations of TCE in aqueous solution.

After normalizing each concentration-specific data set by its respective negligible-turbidity TCE Raman line intensity, as shown in FIG. 10, it is clear that the observed reduction in counts with increasing turbidity can again be described by a negative natural logarithmic function. However, the coefficients and constants in the equation are notably different from those obtained for the nitrate analysis. The difference stems from the need to employ a more powerful laser source (20 μJ vs. 3 μJ) and more sensitive data acquisition system (PMT vs. CCD) to work with TCE, which leads to a fundamentally different transfer function for the system. This implies that an equipment specific calibration will be useful to interpret the effect of turbidity on any particular target analyte.

Although at any given TCE concentration turbidity level can be expected to influence the Raman return of the water line in the same manner as the TCE Raman line, the water Raman line cannot be used as an intrinsic calibration in this case due to the interactions that are known to occur between the hydrogen bonds in water and the chlorine comprising the chlorinated solvent. Thus an alternative technique (such as described above for the case of analyte affecting the Raman line intensity of the solvent) to determine in-situ turbidity would be helpful to identify the appropriate correction factor from FIG. 7 that could be employed to adjust field measurements.

One alternative includes observations of diffuse reflectance to interpret the turbidity level of turbid media. Measured diffuse reflectance spectra contain information describing the scattering and absorption of light in a particular turbid medium; and the intensity of the diffuse reflectance tends to be inversely related to the turbidity of the sampled media. In addition, there are a range of single-sided turbidity meters available that could readily be employed in-situ to acquire direct measures of the turbidity level. Direct turbidity observations, or inferred levels of turbidity developed from diffuse reflectance observations, combined with a turbidity influence curve such as that shown in FIG. 10, thus offer means to initiate the correction of Raman data obtained in the presence of analytes that alter the Raman response of water.

While many solvents exist in many field situations, the methods described here can be used when the solvent is water. Water tends to be a primary solvent in many different environmental contexts and industrial operations, and Raman signatures of water tend to be shifted from the Raman signatures of many chemicals of interest.

Many analytes can be present in the turbid solutions described above. However, we can focus on one analyte at a time or analyze the Raman signature of the turbid solution for many analytes as long as we have calibration data sets corresponding to analytes of interest. It should be recognized that in some complex solutions where Raman signatures overlap (that is, overlap of Raman lines for solvents and analytes or overlap of several analytes or overlap of several solvents) deconvolving techniques such as principal component analyses known to those skilled in the art can be employed.

It should be noted that in the methods described above for an analyte (or analytes) is (are) specified before making a Raman measurement, so that that the Raman measurement equipment used can be adjusted to generate a Raman line intensity data for the solvent and the chosen analyte or analytes.

It is to be further recognized that methods described in this disclosure for correcting for turbidity effects in Raman observations are applicable in practical monitoring scenarios in the field without the need for "pass through" optical observations, and do not need for a priori modeling thus enabling corrections in "real time" thereby accounting for in-situ changes. These methods also eliminate the need to deeply penetrate the sample with radiation or analyze large areas, and hence these methods enable corrections in "real time" to account for in-situ changes, and also enable targeted, single-sided optical observations.

It is also to be noted that the analyte or analytes need not be specified. In such a case, the full spectrum of a finger print region of the Raman signatures from the turbid solution can be obtained and analyze by relating fundamental knowledge of the bonds in compounds to what is observed in the Raman signature.

In various embodiments of the present invention there is no requirement to obtain a test sample of the solution being tested. Instead, various embodiments contemplate the notion of an "in-situ" measurement. In such cases, the technician will put the sensing equipment right into the natural setting (e.g., in a well, in a stream, or underground in a soil probe like a cone penetrometer). Thus we are not obtaining a sample, but instead just measuring an unaltered/unprepared environment that is in its natural state. However, one can also obtain a sample of the turbid solution of interest from the field. Thus the turbid solutions that are analyzed for the concentration of an analyte can be from a well, a body of water, a subsurface water environment, an aquifer, a waste water stream, and an industrial process stream. These are to be recognized as non-limiting examples for the source of the turbid solution. The methods described above will also work for samples obtained from the field. Care should be taken that samples so obtained from the field are representative of the field conditions, especially in terms of turbidity.

It should be noted that the turbidity values that can use the methods described here have very wide range. It is expected that the methods described in this disclosure can be used for turbid solutions with turbidly values ranging from 3-300 NTUs. A higher value for the range is possible.

It should be further recognized that the methods described here are convenient for "in-situ" measurements. Further, the methods described are especially suitable where the analyte concentration is low and turbidity values for the solutions are high (40-200 NTUs as a non-limiting range). The methods described here can be used for analyte concentrations as lows a few parts per million and even for analyte concentrations of a few parts for billion.

In several embodiments of this disclosure, reference is made to a Raman line intensity. It is known to those skilled in the art that while a substance can have more than one Raman line, and more than one Raman line may be needed to uniquely assess identify and/or quantify an analyte, a Raman line, or combination of Raman lines, is chosen based on intensity or other considerations. In the embodiments of this disclosure it is possible to use more than one Raman line of a substance for the analysis and the method can be adjusted by those skilled on the art.

As mentioned in this description, a turbid solution can contain more than one analyte. If study of more than one analyte is needed, these methods can be repeated for each analyte of interest. Alternatively, depending on how the Raman measurement unit is adjusted, the Raman signature of the turbid solution can capture Raman line intensities for several analytes. In such cases if corresponding calibration curves for the analytes are available, the methods described in this disclosure can be employed.

While the present disclosure has been described with reference to certain embodiments, it will be apparent to those of ordinary skill in the art that other embodiments and implementations are possible that are within the scope of the present disclosure without departing from the spirit and scope of the present disclosure. Thus, the implementations should not be limited to the particular limitations described. Other implementations may be possible. It is therefore intended that the foregoing detailed description be regarded as illustrative rather than limiting. Thus, this disclosure is limited only by the following claims.

The invention claimed is:

1. A method for measurement of concentration of at least one specified analyte in a solution of unknown turbidity containing a solvent with suspended particles and at least one specified analyte, the method comprising:
   providing the solution of unknown turbidity containing the solvent with suspended particles and at least one specified analyte;
   providing a first calibration data set that relates turbidity of an analyte-free solvent sample to a Raman line intensity for the analyte-free solvent;
   generating Raman signature of the solution and determining a Raman line intensity of the solvent in the solution and a Raman line intensity of the at least one specified analyte in the solution;
   comparing the Raman line intensity of the solvent in the solution to the first calibration data set and determining a turbidity value for the solution;
   providing a second calibration data set that relates turbidity of the at least one specified analyte to a normalized Raman line intensity for the at least one specified analyte;
   determining a turbidity correction factor based on the turbidity value of the solution and the second calibration data set;
   applying the turbidity correction factor to the Raman line intensity for the at least one specified analyte in the solution and calculating a turbidity-corrected Raman intensity for the at least one specified analyte; and
   determining the concentration of the at least one specified analyte in the solution by comparing the turbidity-corrected Raman intensity of the at least one specified analyte to a calibration curve that relates Raman intensity of the at least one specified analyte to concentration of the at least one specified analyte in a solvent with negligible turbidity.

2. The method of claim 1, wherein the analyte-free solvent sample is taken proximate to the solution.

3. The method of claim 1, wherein the solvent is water.

4. The method of claim 3, wherein the analyte-free solvent sample is taken proximate to the solution.

5. The method of claim 3, wherein the solution is from one of a well, a body of water, a subsurface water environment, an aquifer, a waste water stream, and an industrial process stream.

6. The method of claim 5, wherein the solvent is water and the analyte is a nitrate.

7. The method of claim 1, wherein the solvent is water and the at least one specified analyte is a nitrate.

8. The method of claim 1, wherein the solution is from one of a well, a body of water, a subsurface water environment, an aquifer, a waste water stream, and an industrial process stream.

9. The method of claim 1, wherein the solution is a sample, the sample being taken from a body of the solution of unknown turbidity containing the solvent and at least one specified analyte.

10. A method for measurement of concentration of at least one specified analyte in a solution of unknown turbidity with suspended particles with a solvent, the method comprising:
    providing the solution of unknown turbidity with suspended particles containing the solvent and at least one specified analyte;
    generating Raman signature of the solution and determining a Raman line intensity of the at least one specified analyte in the solution;
    providing a calibration data set that relates turbidity of the at least one specified analyte to normalized intensity of a Raman line for the at least one specified analyte;
    measuring the turbidity value of the solution;
    determining a turbidity correction factor based on the turbidity value of the solution and the calibration data set;
    applying the turbidity correction factor to the Raman line intensity for the at least one specified analyte in the solution and calculating a turbidity-corrected Raman intensity for the at least one specified analyte; and
    determining the concentration of the at least one specified analyte in the solution by comparing the turbidity-corrected Raman intensity of the at least one specified analyte to a calibration curve that relates Raman intensity of the at least one specified analyte to concentration of the at least one specified analyte in a solvent with negligible turbidity.

11. The method of claim 10, wherein the solvent is water.

12. The method of claim 11, wherein the solution is taken from one of a well, a body of water, a subsurface water environment, an aquifer, a waste water stream, and an industrial process stream.

13. The method of claim 10, wherein the solvent is water and the analyte is a chlorinated compound.

14. The method of claim 13, wherein the chlorinated compound is trichloroethylene.

15. The method of claim 10, wherein the solution is taken from one of a well, a body of water, a subsurface water environment, an aquifer, a waste water stream, and an industrial process stream.

16. The method of claim 15, wherein the turbidity is measured by a turbidimeter.

17. The method of claim 10, wherein the turbidity measurement is done by a direct method.

18. The method of claim 10, the turbudity measurement is done by an indirect method.

19. The method of claim 10, wherein the turbidity measurement is done by using a diffuse reflectance method.

20. The method of claim 10, the solution is a sample, the sample being taken from a body of the solution of unknown turbidity containing a solvent and at least one specified analyte.

* * * * *